(12) United States Patent
Rosenfeldt et al.

(10) Patent No.: US 7,799,737 B2
(45) Date of Patent: Sep. 21, 2010

(54) USE OF FATTY ALCOHOLS ETHOXYLATES AS PENETRATION PROMOTERS

(75) Inventors: Frank Rosenfeldt, Langenfeld (DE); Peter Baur, Eppstein (DE)

(73) Assignee: Bayer CropScience AG, Monheim (DE)

( * ) Notice: Subject to any disclaimer, the term of this patent is extended or adjusted under 35 U.S.C. 154(b) by 1284 days.

(21) Appl. No.: 10/474,115

(22) PCT Filed: Apr. 2, 2002

(86) PCT No.: PCT/EP02/03618

§ 371 (c)(1),
(2), (4) Date: Mar. 29, 2004

(87) PCT Pub. No.: WO02/098230

PCT Pub. Date: Dec. 12, 2002

(65) Prior Publication Data

US 2004/0157743 A1 Aug. 12, 2004

(30) Foreign Application Priority Data

Apr. 11, 2001 (DE) ................................ 101 18 076

(51) Int. Cl.
*A01N 25/24* (2006.01)
*A01N 25/30* (2006.01)
*A01N 25/12* (2006.01)

(52) U.S. Cl. ..................................................... 504/100

(58) Field of Classification Search ................... 504/100
See application file for complete search history.

(56) References Cited

U.S. PATENT DOCUMENTS

| | | | |
|---|---|---|---|
| 5,328,693 A | 7/1994 | Horstmann et al. | 424/405 |
| 6,274,570 B1 * | 8/2001 | Vogt et al. | 514/89 |
| 6,541,425 B1 * | 4/2003 | Ernst et al. | 504/312 |
| 6,716,443 B1 | 4/2004 | Abribat et al. | 424/405 |
| 2003/0224936 A1 * | 12/2003 | Kretzschmar | 504/100 |

FOREIGN PATENT DOCUMENTS

| | | | |
|---|---|---|---|
| CN | 1187299 | | 7/1998 |
| EP | 0 579 052 | | 1/1994 |
| EP | 0 596 316 | | 5/1994 |
| FR | 9913842 | * | 10/1999 |
| WO | 97/25863 | | 7/1997 |
| WO | 97/49284 | | 12/1997 |
| WO | WO9926472 | * | 6/1999 |
| WO | WO/00/54568 | * | 9/2000 |

OTHER PUBLICATIONS

Baur et al., Penetration of an ethoxylated fatty alcohl surfactant across leaf cuticles as affected by concentration, additives, and humidity, Journal of Plant Diseases and Protection, 1997, 104(4),380-393.*

Schreiber ,Pesticide Science, Sep. 1995,John Wiley and Sons, vol. 45, issue 1, pp. 1-11.*

Baur et al., Pesticide Science, 1999, volume/edition 55, pp. 831-842.*

Database CA 'Online! Chemical Abstracts Service, Columbus, Ohio, US; retrieved from STN-International, Database accession No. 133:248388 CA XP002214095 Zusammenfassung & CN 1 245 643 A (Pesticide Formulations Engineering Technology Center) Mar. 1, 2000.

Database CA 'Online! Chemical Abstracts Service, Columbus, Ohio, US; retrieved from STN-International, Database accession No. 133:204213 CA XP002214096 Zusammenfassung & CN 1 242 940 A (Peop. Rep. China) Feb. 2, 2000.

Database Biosis 'Online! Biosciences Information Service, Philadelphia, PA, US; May 2000 Schoenherr J et al: "Rates of cuticular penetration of 1-naphthylacetic acid (NAA) as affected by adjuvants, temperature, humidity and water quality." Database accession No. PREV200000276498 XP002214092 Zusammenfassung & Plant Growth Regulation, Bd. 31, Nr. 1-2, May 2000, Seiten 61-74, ISSN: 0167-6903.

Database Biosis 'Online! Biosciences Information Service, Philadelphia, PA, US; Feb. 1999 Baur Peter: Surfactant effects on cuticular pentration of neutral polar compounds: Dependence on humidity and temperature. Database accession No. PREV199900143947 XP002214093 Zusammenfassung & Journal Of Agricultural and Food Chemistry, Bd. 47, Nr. 2, Feb. 1999, Seiten 753-761, ISSN: 0021-8561.

Database Biosis 'Online! Biosciences Information Service, Philadelphia, PA, US; Jul. 1997 Baur P et al: Penetration of an ethoxylated fatty alcohol surfactant across leaf cuticles as affected by concentration, additives, and humidity. Database accession No. PREV19900088580 XP002214094 Zusammenfassung & Zeitschrift Fuer Pflanzenkrankheiten Und Pflanzenschutz, Bd. 104, Nr. 4, Jul. 1997 Seiten 380-393, ISSN: 0340-8159.

Recent Res. Devel. in Agricultural & Food Chem., 2, (month unavailable) 1998, pp. 809-837, "Mechanistic aspects of foliar penetration of agrochemicals and the effect of adjuvants" by P. Baur.

* cited by examiner

Primary Examiner—Johann R Richter
Assistant Examiner—Courtney Brown
(74) Attorney, Agent, or Firm—Baker Donelson Bearman, Caldwell & Berkowitz, PC

(57) ABSTRACT

This invention relates to fatty alcohol ethoxylates of the formula

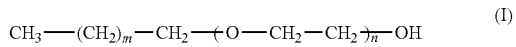

in which
m represents average values from 8.0 to 13.0 and
n represents average values from 6.0 to 17.0, that are highly suitable for use as penetrants for insecticidally active neonicotinyls when employed in amounts such that they are present in the commercial formulations in concentrations from 0.1 to 30% by weight and such that the weight ratio of neonicotinyl to fatty alcohol ethoxylate is from 1:0.1 to 1:2.0.

10 Claims, No Drawings

USE OF FATTY ALCOHOLS ETHOXYLATES AS PENETRATION PROMOTERS

The present invention relates to the novel use of fatty alcohol ethoxylates as penetrants for certain active compounds having insecticidal properties.

It is generally known that many agrochemically active compounds, in particular those having systemic action, have to penetrate into the plant to be able to unfold their activity evenly throughout the plant. Thus, when the active compound is taken up via the leaves, the active compounds have to overcome the penetration barrier of the cuticle. Moreover, it is important that the agrochemically active compounds penetrate rapidly, distributed over a surface which is as large as possible, into the plant, since there may otherwise be the risk that the active components are washed off by rain.

Furthermore, it is generally known that some additives used in crop protection compositions, such as, for example, surfactants, mineral oils and vegetable oils, promote penetration of agrochemically active compounds into the plant and are thus able to enhance the activity of the active compounds. In the individual case, the additives may increase wettability, lead to a better distribution of the spray coating on the surface (=spreading) of the plant, increase the availability of the active compound in the dried spray residue by partial dissolution or directly promote penetration of the active compound through the cuticle. Here, the additives are either incorporated directly into the formulation—which is only possible up to a certain percentage—or added it to the spray liquor in question using the tank mix method.

Furthermore, it is already known that fatty alcohol ethoxylates can be used as penetrants for numerous agrochemically active compounds (cf. EP-A 0 579 052 and Recent Res. Devel. in Agricultural & Food Chem. 2 (1998), 809-837). However, it is disadvantageous that the desired effect is only observed when the formulation used has a relatively high content of fatty alcohol ethoxylate.

It has now been found that fatty alcohol ethoxylates of the formula

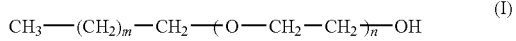

(I)

in which
 m represents average values from 8.0 to 13.0,
 n represents average values from 6.0 to 17.0, can be used as penetrants for insecticidally active compounds from the group of the neonicotinyls when they are present in commercial formulations in concentrations from 0.1 to 30% by weight, the weight ratio of insecticidally active compound from the group of the neonicotinyls to fatty alcohol ethoxylate of the formula (I) being from 1:0.1 to 1:2.0.

Accordingly, the invention relates to the use of fatty alcohol ethoxylates of the formula (I) for the stated purpose. Moreover, the invention relates to plant treatment compositions comprising
 from 0.1 to 30% by weight of fatty alcohol ethoxylate of the formula (I),
 from 1 to 50% by weight of active compound from the group of the neonicotinyls,
 from 1 to 80% by weight of dimethyl sulfoxide, N-methylpyrrolidone and/or butyrolactone, and
 from 0 to 20% by weight of additives.

It is extremely surprising that fatty alcohol ethoxylates of the formula (I) are considerably more suitable as penetrants for insecticidally active neonicotinyls than comparable substances used for the same purpose. It is also unexpected that even very low concentrations of fatty alcohol ethoxylate of the formula (I) are sufficient to achieve the desired effect.

The use according to the invention of fatty alcohol ethoxylates of the formula (I) has a number of advantages. Thus, these fatty alcohol ethoxylates are products which can be handled without any problems and are available even in relatively large amounts. Moreover, they are biodegradable and permit the effectiveness of the application of neonicotinyls to be increased considerably.

The formula (I) provides a general definition of the fatty alcohol ethoxylates which can be used according to the invention. These fatty alcohol ethoxylates are, in general, mixtures of substances of this type having different chain lengths. Accordingly, for the indices m and n, average values are obtained which may not be integers.

Preference is given to using fatty alcohol ethoxylates of the formula (I) in which
 m represents average values from 9.0 to 12.0
 n represents average values from 7.0 to 9.0.

Very particular preference is given to the fatty alcohol ethoxylate of the formula (I) in which
 m represents the average value 10.5 and
 n represents the average value 8.4.

The fatty alcohol ethoxylates of the formula (I) and their use as surfactants are already known.

In the present context, insecticidally active neonicotinyls is preferably to be understood as meaning the following substances:

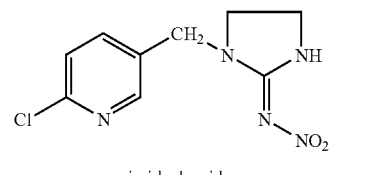

imidacloprid

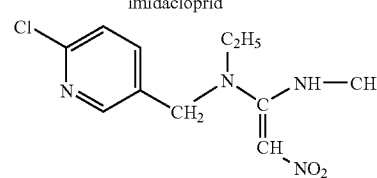

nitenpyram

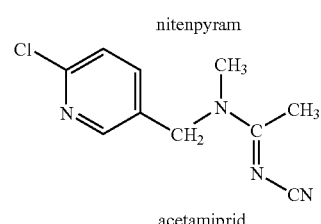

acetamiprid

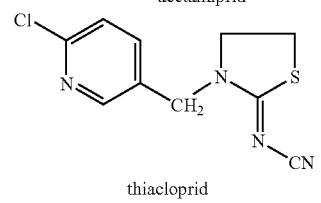

thiacloprid

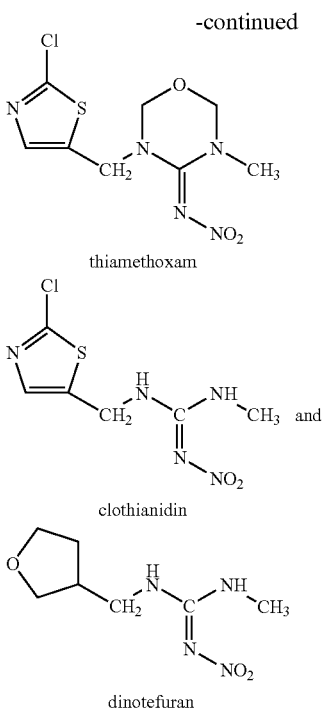

thiamethoxam clothianidin dinotefuran

The substances mentioned above and their use as insecticides are known.

Suitable additives which may be contained in the plant treatment compositions according to the invention are further agrochemically active compounds, and crystallization inhibitors, wetting agents, emulsifiers and also water.

Suitable agrochemically active compounds are preferably substances having insecticidal, acaricidal and/or fungicidal properties.

Suitable insecticides and/or acaricides are preferably active compounds from the group of the pyrethroids or the ketoenol derivatives. By way of example, the following compounds may be mentioned:
cypermethrin,
deltamethrin,
permethrin,
natural pyrethrum,
fenpropathrin,
cyfluthrin,
β-cyfluthin and also, from the group of the ketoenol derivatives, 3-(2,4-dichlorophenyl)-4-(1,1-dimethyl-propyl-carbonyloxy)-5-spiro-cyclohexyl-3-dihydrofuran-2-one and 3-(2,4,6-trimethylphenyl)-4-(2,2-dimethyl-propyl-carbonyloxy)-5-spiro-cyclopentyl-3-dihydrofuran-2-one.

Suitable fungicides are preferably active compounds from the group of the azoles, the strobilurin derivatives and the amino acid derivatives. By way of example, the following compounds may be mentioned:
tebuconazole,
cyproconazole,
triadimenol,
myclobutanil,
trifloxystrobin,
azoxystrobin,
kresoxim-methyl,
pyraclostrobin, 3-[1-(2-[4-(2-chlorophenoxy)-5-fluoropyrimid-6-yloxy]-phenyl)-1-(methoximino)-methyl]-5,6-dihydro-1,4,2-dioxazine and iprovalicarb.

Suitable crystallization inhibitors which may be present in the plant treatment compositions according to the invention are all substances which may customarily be used in agrochemical compositions for such purposes. By way of preference, mention may be made of N-alkyl-pyrrolidones, such as N-octyl-pyrrolidone and N-dodecylpyrrolidone, furthermore of copolymers of polyvinyl-pyrrolidone and polyvinyl alcohol, such as, for example, the polyvinylpyrrolidone/polyvinyl alcohol copolymer known under the name Luviskol VA 64 (from BASF), furthermore N,N-dimethyl-alkylcarboxamides, such as N,N-dimethyl-decanamide or the N,N-dimethyl-$C_{6-12}$-alkanecarboxamide mixture known under the name Hallcomid® (from Hall Comp.), and furthermore copolymers of ethylenediamine with ethylene oxide and propylene oxide, such as, for example, the product known under the name Synperonic T 304 (from Uniqema).

Suitable wetting agents are all substances which may customarily used for such purposes in plant treatment compositions. By way of preference, mention may be made of alkylphenol ethoxylates, dialkylsulfosuccinates, such as dioctylsulfosuccinate sodium, lauryl ether sulfates and polyoxyethylene sorbitan fatty acid ester.

Suitable emulsifiers are all customary nonionic, anionic, cationic and zwitterionic substances having surface-active properties which are customarily used in agro-chemical compositions. These substances include reaction products of fatty acids, fatty acid esters, fatty alcohols, fatty amines, alkylphenols or alkylarylphenols with ethylene oxide and/or propylene oxide and/or butylene oxide, and their sulfuric acid esters, phosphoric acid monoesters and phosphoric acid diesters, furthermore reaction products of ethylene oxide with propylene oxide, and additionally alkylsulfonates, alkyl sulfates, aryl sulfate, tetra-alkyl-ammonium halides, trialkylaryl-ammonium halides and alkylamine-sulfonates. The emulsifiers can be used individually or else in mixtures. By way of preference, mention may be made of reaction products of castor oil with ethylene oxide in a molar ratio of from 1:20 to 1:60, reaction products of $C_6$-$C_{20}$-alcohols with ethylene oxide in a molar ratio of from 1:5 to 1:50, reaction products of fatty amines with ethylene oxide in a molar ratio of from 1:2 to 1:25, reaction products of 1 mol of phenol with 2 to 3 mol of styrene and 10 to 50 mol of ethylene oxide, reaction products of $C_8$-$C_{12}$-alkylphenols with ethylene oxide in a molar ratio of from 1:5 to 1:30, alkylglycosides, $C_8$-$C_{16}$-alkylbenzene-sulfonic acid salts, such as, for example, calcium, monoethanolammonium, diethanolammonium and triethanolammonium salts.

Examples of nonionic emulsifiers which may be mentioned are the products known under the names Pluronic PE 10 100 (from BASF) and Atlox 4913 (from Uniqema). Also suitable are tristyryl-phenyl ethoxylates. Examples of anionic emulsifiers which may be mentioned are the commercial product from Bayer AG which is known under the name Baykanol SL (=condensate of sulfonated ditolyl ether with formaldehyde), and also phosphated or sulfated tristyryl-phenol ethoxylates, especially Soprophor FLK and Soprophor 4D 384 (from Rhodia).

When fatty alcohol ethoxylates of the formula (I) are used according to the invention, the content of these products can be varied within a certain range. In general, fatty alcohol ethoxylates of the formula (I) are used in such an amount that they are present in the commercial formulations in concentrations from 0.1 to 30% by weight, preferably from 0.5 to 15% by weight. Here, the weight ratio of insecticidally active compound from the group of the neonicotinyls to fatty alcohol ethoxylate of the formula (I) is chosen such that it is generally from 1:0.1 to 1:2.0, preferably from 1:0.2 to 1:0.5.

The content of the individual components in the plant treatment compositions according to the invention can be varied within a certain range. Preference is given to plant treatment compositions in which the concentrations of fatty alcohol ethoxylate of the formula (I) are from 0.5 to 15% by weight,
of active compound from the group of the neonicotinyls are from 2.5 to 30% by weight,
of dimethyl sulfoxide, N-methylpyrrolidone and/or butyrolactone are from 30 to 80% by weight and
of additives are from 0 to 15% by weight.

If the plant treatment compositions according to the invention are ready-to-use products, preference is given to those in which the content of fatty alcohol ethoxylate of the formula (I) is from 0.01 to 0.2% by weight,
of active compound from the group of the neonicotinyls is from 0.001 to 0.03% by weight,
of dimethyl sulfoxide, N-methylpyrrolidone and/or butyrolactone is from 0 to 50% by weight and
of additives is from 0 to 95% by weight.

The plant treatment compositions according to the invention are prepared by mixing the components with each other in the ratios desired in each case. In general, an active compound from the group of the neonicotinyls is initially charged, and the other components are then added with stirring, in any order.

When preparing the plant treatment compositions according to the invention, the temperatures can be varied within a certain range. In general, the compositions are prepared at temperatures from 10° C. to 50° C., preferably at room temperature.

Suitable for preparing the plant treatment compositions according to the invention is an apparatus customarily used for preparing agrochemical formulations.

The plant treatment compositions according to the invention can be applied either as such or after prior dilution with water or other diluents, i.e., for example, as emulsions, suspensions, solutions or aerosols. Application is carried out by customary methods, i.e., for example, by spraying, watering, atomizing, injecting or spreading.

The application rate of the plant treatment compositions according to the invention can be varied within a relatively wide range. It depends on the particular active compounds contained in the formulations, and their concentration.

With the aid of the plant treatment compositions according to the invention, it is possible to apply neonicotinyls in a particularly advantageous manner to the plants and/or their habitat. Here, the tendency of solid active compounds to crystallize is reduced, the penetration power of the active compounds is enhanced and, compared to customary formulations, the biological activity of the active components is increased.

The invention is illustrated by the following examples.

PREPARATION EXAMPLES

Example 1

To prepare a formulation,
20 g of imidacloprid are, with stirring at room temperature, admixed successively with 5 g of the copolymer of polyvinylpyrrolidone and polyvinyl alcohol known under the name Luviskol VA 64 (from BASF),
10 g of the fatty alcohol ethoxylates of the formula (I) known under the name Genapol C-100 (from Clariant), in which
m represents the average value 10.5
n represents the average value 8.4 and
65 g of N-methyl-pyrrolidone.
After the addition has ended, stirring at room temperature is continued for 5 minutes. This gives a homogeneous liquid.

Example 2

To prepare a formulation,
7 g of imidacloprid are, with stirring at room temperature, admixed successively with 5 g of the copolymer of polyvinylpyrrolidone and polyvinyl alcohol known under the name Luviskol VA 64 (from BASF),
10 g of the fatty alcohol ethoxylates of the formula (I) known under the name Genapol C-100 (from Clariant), in which
m represents the average value 10.5
n represents the average value 8.4,
2.5 g of cyfluthrin and
75.5 g of N-methyl-pyrrolidone.
After the addition has ended, stirring at room temperature is continued for 5 minutes. This gives a homogeneous liquid.

Comparative Example A

To prepare a formulation,
20 g of imidacloprid are, with stirring at room temperature, admixed successively with 5 g of the copolymer of polyvinylpyrrolidone and polyvinyl alcohol known under the name Luviskol VA 64 (from BASF),
10 g of diethyl sebacate,
10 g of castor oil ethoxylate and
55 g of N-methylpyrrolidone.
After the addition has ended, stirring at room temperature is continued for 5 minutes. This gives a homogeneous liquid.

Comparative Example B

To prepare a formulation,
20 g of imidacloprid
are, with stirring at room temperature, admixed successively with
5 g of the copolymer of polyvinylpyrrolidone and polyvinyl alcohol known under the name Luviskol VA 64 (from BASF),
10 g of a mixture of
5% by weight of N,N-dimethyl-hexanecarboxamide,
50% by weight of N,N-dimethyl-octanecarboxamide,
40% by weight of N,N-dimethyl-decanecarboxamide and
5% by weight of N,N-dimethyl-dodecanamide,
10 g of castor oil ethoxylate and
55 g of N-methylpyrrolidone.

After the addition has ended, stirring at room temperature is continued for 5 minutes. This gives a homogeneous liquid.

Comparative Example C

To prepare a formulation,
20 g of imidacloprid
are, with stirring at room temperature, admixed successively with
5 g of the copolymer of polyvinylpyrrolidone and polyvinyl alcohol known under the name Luviskol VA 64 (from BASF),
10 g of polyoxyethylene sorbitan monooleate having on average 20 oxyethylene units per molecule,
10 g of castor oil ethoxylate and
55 g of N-methylpyrrolidone.

After the addition has ended, stirring at room temperature is continued for 5 minutes. This gives a homogeneous liquid.

Use Example I

Determination of the penetration of imidacloprid into barley plants.

Active Compound Preparation

To prepare a ready-to-use preparation of active compound, in each case 1 part by weight of the formulations stated in the examples above was diluted with water such that a spray liquor containing 200 mg of imidacloprid per litre was obtained.

Application Rate

Per plant, in each case 3 µl of ready-to-use preparation of active compound and a defined, in each case identical amount of radiolabelled imidacloprid were used.

Plants

The plants used were 14 day-old barley plants of the cultivar Tapir which had been grown in vermiculite and were in the 2-leaf stage.

Point of Application

3 µl of the ready-to-use preparation of active compound were in each case applied onto the first leaf, at a distance of 5.5 cm to the tip of the leaf.

Duration of the Experiment 24 or 48 hours from the time of application to the removal by washing.

Repetitions 5 repetitions per preparation of active compound.

Climate 12 hours of light at 22-23° C. and 55-60% relative atmospheric humidity; 10 hours of darkness at 15° C. and 80% relative atmospheric humidity, and twice 1 hour each of twilight at the same climate as in the period before.

Controls

In each case 3 µl of ready-to-use preparation of active compound were pipetted directly into a scintillation bottle. 5 repetitions per preparation of active compound.

Preparation

The second leaves of the barley plants at the 2-leaf stage, freshly grown in a greenhouse, were cut off. The remaining leaves of the horizontally arranged plants were then fixed with the aid of microscope slides such that the points of application on the leaves in an area of 2 cm were not twisted. Following their preparation, the ready-to-use preparations of active compound were stirred at room temperature for 60 minutes.

Application and Work-Up

In each case 3 µl of the preparation of active compound were applied onto the middle of a leaf. The plants were then allowed to rest until the preparation of active compound had dried on. At the same time, as a control, in each case 3 µl of the preparation of active compound were pipetted directly into a scintillation bottle. This control was carried out in 5 repetitions. Immediately afterwards, the other preparations of active compounds and plants were subjected to the same procedure. Following application, a temperature of 21-22° C. and a relative atmospheric humidity of 70% was maintained in the laboratory.

After all of the preparations of active compounds that had been applied had dried on, the treated plants were placed in a climatized chamber for 22 or 46 hours. 24 or 48 hours after the application of the preparations of active compounds, the leaves of all plants were once more fixed using slides. The entire surface of the point of application was then covered with 30 µl of a 5% strength solution of cellulose acetate in acetone. After the solution had dried on completely, the cellulose acetate film formed was in each case removed and placed into a scintillation bottle. In each case, 1 ml of acetone was then added to the cellulose acetate film. The samples remained at room temperature in closed vessels until the substance contained therein had been dissolved. Thereafter, in each case 2 ml of scintillation liquid were added. Beforehand, the tips of the leaves had been cut off in one piece and placed into cardboard hats. Cardboard hats and content were dried at 50° C. for 16 hours. The radioactivity of all samples was then determined by liquid and incineration scintillation. The values obtained are used to calculate the percentage of uptake of active compound and translocation. 0% means that no active compound has been taken up and translocated; 100% means that all of the active compound has been taken up and translocated.

The test results are shown in the table below.

TABLE I

| Formulation According to example | Determination of the penetration of imidacloprid into barley plants | |
|---|---|---|
| | Uptake of active compound and translocation in % after | |
| | 24 hours | 48 hours |
| Known: | | |
| (A) | 3.8 | 4.8 |
| (B) | 2.6 | 6.4 |
| (C) | <2 | <5 |
| According to the invention: | | |
| (1) | 42.7 | 68.6 |

The results show that the formulation according to the invention penetrates considerably better than the formulations used for comparison.

What is claimed is:

1. A method of promoting penetration of plants by insecticidally active neonicotinyls comprising applying to a plant a composition comprising
    (a) from 0.1 to 30% by weight, based on the composition, of a fatty alcohol ethoxylate of formula (I)

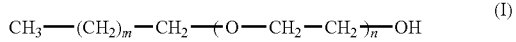

in which
        m represents an average value from 8.0 to 13.0, and
        n represents an average value from 6.0 to 17.0, and
    (b) an insecticidally active neonicotinyl at a weight ratio of neonicotinyl to fatty alcohol ethoxylate of from 1:0.1 to 1:2.0.

2. A method according to claim 1 wherein the insecticidally active neonicotinyl is imidacloprid, nitenpyram, acetamiprid, thiacloprid, thiamethoxam, clothianidin, or dinotefuran.

3. A plant treatment composition comprising
    (a) from 0.1 to 30% by weight, based on the composition, of a fatty alcohol ethoxylate of formula (I)

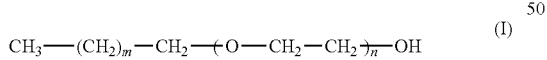

in which
        m represents an average value from 8.0 to 13.0, and
        n represents an average value from 6.0 to 17.0, and
    (b) an insecticidally active neonicotinyl at a weight ratio of neonicotinyl to fatty alcohol ethoxylate of from 1:0.1 to 1:2.0.

4. A plant treatment composition according to claim 3 comprising
    (a) from 0.1 to 30% by weight, based on the composition, of a fatty alcohol ethoxylate of formula (I),
    (b) from 0.1 to 50% by weight, based on the composition, of an insecticidally active neonicotinyl,
    (c) from 1 to 80% by weight, based on the composition, of dimethyl sulfoxide, N-methylpyrrolidone, butyrolactone, or a mixture thereof, and
    (d) from 0 to 20% by weight, based on the composition, of one or more additives.

5. A plant treatment composition according to claim 4 wherein, for the fatty alcohol ethoxylate of formula (I),
    m represents an average value from 9.0 to 12.0, and
    n represents an average value from 7.0 to 9.0.

6. A plant treatment composition according to claim 4 wherein, for the fatty alcohol ethoxylate of formula (I),
    m represents an average value of 10.5, and
    n represents an average value of 8.4.

7. A plant treatment composition according to claim 4 wherein the insecticidally active neonicotinyl is imidacloprid, nitenpyram, acetamiprid, thiacloprid, thiamethoxam, clothianidin, or dinotefuran.

8. A plant treatment composition according to claim 4 wherein the one or more additives are agrochemically active compounds, crystallization inhibitors, wetting agents, emulsifiers, water, or mixtures thereof.

9. A plant treatment composition according to claim 4 comprising
    (a) from 0.5 to 15% by weight, based on the composition, of a fatty alcohol ethoxylate of formula (I),
    (b) from 2.5 to 30% by weight, based on the composition, of an insecticidally active neonicotinyl,
    (c) from 30 to 80% by weight, based on the composition, of dimethyl sulfoxide, N-methylpyrrolidone, butyrolactone, or a mixture thereof, and
    (d) from 0 to 15% by weight, based on the composition, of one or more additives.

10. A ready-to-use plant treatment composition comprising
    (a) a fatty alcohol ethoxylate of formula (I)

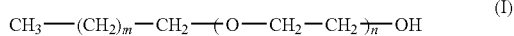

in which
        m represents an average value from 8.0 to 13.0, and
        n represents an average value from 6.0 to 17.0, and
    (b) from 0.001 to 0.03% by weight, based on the composition, of an insecticidally active neonicotinyl at a weight ratio of neonicotinyl to fatty alcohol ethoxylate of from 1:0.1 to 1:2.0,
    (c) from 0 to 50% by weight, based on the composition, of dimethyl sulfoxide, N-methylpyrrolidone, butyrolactone, or a mixture thereof, and
    (d) from 0 to 95% by weight, based on the composition, of one or more additives.

* * * * *